(12) United States Patent
Molitor et al.

(10) Patent No.: US 8,028,592 B2
(45) Date of Patent: Oct. 4, 2011

(54) ELECTRONIC METERING APPARATUS FOR METERING LIQUIDS

(75) Inventors: Peter Molitor, Henstedt-Ulzburg (DE); Karl-Friedrich Andres, Bargteheide (DE); Peter Schmidt, Lübeck (DE)

(73) Assignee: Eppendorf AG, Hamburg (DE)

( * ) Notice: Subject to any disclaimer, the term of this patent is extended or adjusted under 35 U.S.C. 154(b) by 544 days.

(21) Appl. No.: 11/833,614

(22) Filed: Aug. 3, 2007

(65) Prior Publication Data

US 2008/0034898 A1 Feb. 14, 2008

(30) Foreign Application Priority Data

Aug. 9, 2006 (DE) .......................... 10 2006 037 213

(51) Int. Cl.
*B01L 3/02* (2006.01)
*B67D 99/00* (2010.01)

(52) U.S. Cl. ............... 73/864.16; 73/863.01; 73/864.14; 222/23; 222/63

(58) Field of Classification Search ............... 73/864.16, 73/864.14, 864.18, 863.32, 863.01–863.03; 222/14, 63, 23
See application file for complete search history.

(56) References Cited

U.S. PATENT DOCUMENTS

| | | | |
|---|---|---|---|
| 4,671,123 A | | 6/1987 | Magnussen, Jr. et al. |
| 5,271,527 A | * | 12/1993 | Haber et al. ................ 222/43 |
| 6,739,478 B2 | * | 5/2004 | Bach et al. .................. 222/1 |
| 2004/0099067 A1 | * | 5/2004 | Chen et al. ............. 73/863.32 |
| 2005/0006410 A1 | * | 1/2005 | Bach et al. ................ 222/309 |
| 2005/0194407 A1 | * | 9/2005 | Bach ........................ 222/309 |
| 2005/0255006 A1 | * | 11/2005 | Romaguera ............... 422/100 |
| 2007/0093752 A1 | * | 4/2007 | Zhao et al. ................. 604/131 |
| 2008/0210023 A1 | * | 9/2008 | Telimaa et al. ........... 73/864.18 |
| 2008/0257907 A1 | * | 10/2008 | Reimers ...................... 222/52 |

FOREIGN PATENT DOCUMENTS

| | | |
|---|---|---|
| DE | 35 86 289 T2 | 6/1996 |
| DE | 35 88 071 T2 | 6/1996 |
| DE | 102004038962 A1 * | 2/2006 |
| EP | 0 656 229 A1 | 10/1994 |
| EP | 0 864 364 A2 | 3/1998 |

(Continued)

OTHER PUBLICATIONS

Brandt GmbH & Co KG "Transferpette electronic", Jul. 2003, 132 pages (pp. 35-66 in English).
Search Report for EP 10013208 mailed Feb. 2, 2011, (in German).

*Primary Examiner* — Thomas P Noland
(74) *Attorney, Agent, or Firm* — Vidas, Arrett & Steinkraus (57) ABSTRACT

An electronic metering apparatus for metering liquids, with a longitudinal, handleable housing, a drive, arranged in the housing, with an electric motor, at least one displacer device, arranged in the housing or being capable to be arranged on the same, with a displacer element, which is connected to the drive and/or connectable to the same, at least one holding device on the bottom end of the housing for holding a pipette point or a syringe, at least one electric operational control in or on the housing, at least one electric information device in or on the housing, an electric control unit arranged in the housing, which is connected to the electric motor, the electric operational control and the electric information device, and which controls the information device depending on the position and/or previous changes of the position of the displacer element, in order to put out an information concerning the next reasonable dislocation of the displacer element, and an electric power supply.

24 Claims, 4 Drawing Sheets

FOREIGN PATENT DOCUMENTS

| WO | 94/03222 | 2/1994 |
| WO | 00/51738 | 9/2000 |
| WO | 2005/052781 | 6/2005 |
| WO | 2005/079989 | 9/2005 |

\* cited by examiner

ELECTRONIC METERING APPARATUS FOR METERING LIQUIDS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to an electronic metering apparatus for metering liquids.

Electronic metering apparatuses for metering liquids have a drive with an electric motor and a displacer device driven by this motor, which comprises a cylinder with a plunger arranged movable therein, for instance. The displacer device is communicatingly connected with a replaceable pipette point, for instance. By means of the displacer device, an air cushion is dislocated, which aspirates liquid into the pipette point and ejects it from the same, respectively. In difference to these air, cushion pipettes, direct displacement pipettes have a replaceable syringe, which aspirates and ejects liquid, respectively. Pipette points and syringes are preferably disposable objects for single use, made from a plastic material.

Further, electronic metering apparatuses are in the state of the art, in which different modes of operation can be selected, like pipetting, dispensing and titrating, for instance. In these metering apparatuses, different parameters may be settable, the liquid volume to be picked up and to be delivered when pipetting, the liquid volume to be picked up and the liquid volumes to be delivered when dispensing or titrating and the plunger speeds when picking up and delivering the liquid, for instance.

Known electronic metering apparatuses have a plurality of operational controls, by which the mode of operation of the metering apparatus is selected, the respective parameters are set and the operation of the metering apparatus is controlled in particular. The handling of the known metering apparatuses is awesome. Furthermore, it is disadvantageous that the control of delivering and pickup of liquid takes place via one single button, which must be actuated in a predetermined manner for releasing and stopping the plunger movement, respectively, so that the operation of electronic metering apparatuses is strongly different from that of manual metering apparatuses.

In the operation, errors can occur because the user does not recognise the next reasonable operation step.

Departing from this, the present invention is based on the objective to provide an electronic metering apparatus which facilitates the operation for the user.

The objective is resolved by the electronic metering apparatus according to claim 1. Advantageous embodiments of the metering apparatus are indicated in the subclaims.

BRIEF SUMMARY OF THE INVENTION

An electronic metering apparatus for metering liquids has a longitudinal, handleable housing, a drive, arranged in the housing, with an electric motor, at least one displacer device, arranged in the housing or being capable to be arranged on the same, with a displacer element, which is connected to the drive and/or connectable to the same, at least one holding device on the bottom end of the housing for holding a pipette point or a syringe, at least one electric operational control in or on the housing, at least one electric information device in or on the housing, an electric control unit arranged in the housing, which is connected to the electric motor, the electric operational control and the electric information device, and which controls the information device depending on the position and/or previous changes of the position of the displacer element, in order to put out an information concerning the next reasonable dislocation of the displacer element, and an electric power supply.

In the metering apparatus according to the present invention, the next reasonable dislocation of the displacer element or the next reasonable operation step is indicated to the user through the electric information device. As a result, the user may better recognise the next reasonable operation step. Thus, the operation of the metering apparatus is facilitated and error-free metering is promoted.

For instance, the displacer device is a displacer chamber with a membrane-like formed wall, the volume of which can be changed by dislocating the membrane. According to one embodiment, the displacer device comprises a cylinder with a plunger arranged to be movable alongside thereof. A displacer device with plunger and cylinder arranged in the housing can be communicatingly connected with the pipette point. When the displacer device having plunger and cylinder can be arranged on the housing, it is a syringe.

The holding device is a cone or cylinder, e.g., onto which a pipette point with a corresponding opening can be pushed up. According to another embodiment, the holding device has gripping devices for gripping a flange on a cylinder and a collar on a plunger of a syringe, like it is described in EP 0 656 229 B1, the entire contents of which is incorporated herein by reference, for instance, the expositions of which relating to these topics are incorporated into the present application by reference.

The metering apparatus has an electric power supply for supplying all the electric devices of the metering apparatus, in particular for the supply of the electric motor, the mode key, the parameter keys, the control keys, the display device and the control unit. The power supply is a mains adapter for instance, at least one accumulator (optionally with charging device) or at least one battery.

The metering apparatus can be retroactively equipped with a pipette point or a syringe. According to one embodiment, the metering apparatus comprises a pipette point or syringe.

The information device can be realised in various ways. Embraced in the scope of the invention is the realisation as an acoustic signal emitter, which emits different sounds or sound sequences or which performs a voice output, depending on the next reasonable dislocation of the displacer element. Further embraced are realisations in which the information device comprises an electric-optic device. The electric-optic device is a display device for instance, a LCD-, OLED- or other display. The display device is arranged on the upper end of the housing, for instance, on the upper side of a housing head in particular. In particular, a display device arranged on the upper side of the housing can additionally serve for the indication of metering volumes, plunger speeds and so on.

According to a particularly simple and effective embodiment, the electric-optic device comprises at least one electric light source. According to a further electric embodiment, the light source is at least one LED.

The information device can be arranged in or on the housing in different manners. According to one embodiment, the information device comprises electric light sources arranged consecutively one after the other in the longitudinal direction of the housing shaft. The electric light sources arranged consecutively one after the other in the longitudinal direction permit obvious information whether the displacer device makes a delivery or a pickup of liquid at the next reasonable extension of the displacer element. For this purpose, the light source next to the pipette point or syringe is switched on at the liquid delivery, for instance, or the light sources are consecutively switched on such that the light wanders towards the pipette point or syringe. By switching on the electric light sources in the reverse direction, the pickup of liquid through the pipette point or syringe is visualised.

According to one embodiment, the electric-optic device is arrow-shaped and points into the longitudinal direction of the housing. An arrow-shaped light source is realised by one or more LED's, for instance, which are accommodated in the housing below an arrow-shaped window.

According to a further embodiment, two arrow-shaped electric-optic devices are directed away from each other in order to visualise the pickup and delivery of liquid.

According to a further embodiment, the electric information device is arranged on the bottom end of the housing. With an electric-optic information source in particular, this permits a very good recognisability through the user, which observes the delivery position of the pipette point or syringe in metering processes, and thus has the bottom end of the housing in her/his field of vision.

According to one embodiment, there is an electric-optic display device with a display surface observable from the outside. The electric display device serves for the indication of metering volumes, plunger speeds, and so on, for instance. In addition, it may be used as an electric information device, as has been explained above.

According to one embodiment, the electric information device is arranged on the outer side of the housing on which the electric operational control and/or the electric display device is/are arranged. Thus, the operational control and/or the display device are advantageously situated on that side of the housing which the user looks at when metering. According to a further embodiment, the metering apparatus has an angled housing head on the upper end of a longitudinal housing shaft and it has the electric operational control and/or the electric display device on the housing head. Preferably, the electric information device is located on the bottom end of the housing shaft.

According to an embodiment which further facilitates the operation, the metering apparatus has an electric mode key (18) and an electric parameter key (19) for changeover between different menus, a pair, of electric control keys, arranged next to each other, for navigation in the menus, setting of parameters and controlling the dislocation of the displacer element, wherein the two control keys control the navigation in the menus, the setting of parameters and the dislocation of the displacer element in different directions, an electronic display device for displaying menus and parameters, wherein the electric control unit is connected to the electric motor, the electric mode key, the electric parameter key, the electric control keys, and the electric display device, and controls the display of menus and parameters by the display device as well as the dislocation of the displacer element corresponding to the actuation of the mode key, the parameter key and the control keys.

In this embodiment, the electric operational control comprises the electric mode key, the electric parameter key and the electric control keys. The changeover between the different menus is controlled by means of the electric mode key and the electric parameter key. The navigation in the menus and the setting of parameters takes place with the aid of the electric control keys. With the term "navigation", the movement from one menu item to another menu item is meant, which is indicated by a pointer pointing towards the menu item or by accentuation of the menu item, for instance. The electric control keys are also used for controlling the movement of the displacer element. In this, by actuating the one control key, the navigation in the menus, the setting of parameters and the dislocation of the displacer element in one direction, and by actuating the other control key, the navigation in the menus, the setting of parameters and the dislocation of the displacer element in the other direction is controlled. With the aid of the display device, the user can observe the menus. As the case may be, he/she can recognise the actual operating condition of the metering apparatus, a selected mode of operation and set parameters, for instance.

The metering apparatus has a small number of operational controls. Due to the combination of sparse operational controls with a display device, an intuitional and self-explaining operation by the user is achieved. Through the fact that the actuation of the one control key controls the pickup, and the actuation of the other control key controls the delivery of liquid, the user can change the direction of the movement of the displacer element at any deliberate point of time. Through this, for instance, picking up supernatants, stopping the pickup and continuing the pickup, gel loading, stopping the delivery and continuing the delivery, repeating the overblow stroke for blowing out residual amounts of liquids and so on is made possible or facilitated, respectively.

According to one embodiment, the control unit controls the display by the display device of submenus concerning certain modes of operation of the metering apparatus and of a main menu, comprising plural modes of operation, corresponding to the actuation of the mode key and the parameter key, for instance. The submenus are related to one or several of the modes of operation pipetting, dispensing, manual pipetting, calibrating, set-up, titrating, and automatic dispensing, gel-loading, pipetting and mixing. The main menu shows all the modes of operation and makes a selection possible. Thus, with the aid of the main menu, the user can select a mode of operation of the metering apparatus.

According to one embodiment, upon actuation of the mode key, the control unit controls the changeover from a submenu concerning one certain mode of operation of the metering apparatus into a main menu concerning plural modes of operation of the metering apparatus and/or the changeover from the aforementioned main menu into a submenu concerning one certain mode of operation of the metering apparatus with selectable menu items and/or the changeover from the aforesaid submenu into a submenu concerning the same mode of operation, in which a parameter of a selected menu item can be set, and/or the changeover with transfer of a set parameter from the aforesaid submenu into the submenu concerning the same mode of operation with selectable menu items.

Thus, by actuating the mode key it is possible to reach a main menu from a submenu for a certain mode of operation, which main menu is concerning plural modes of operation, all the modes of operation in particular in which the metering apparatus can work. In the main menu, the user can select a mode of operation. Further, by actuating the mode key it can be changed over from the main menu to a submenu for a certain mode of operation, in which individual menu items are selectable. Furthermore, by actuating the mode key, a changeover to a menu can be executed in which the parameters of selected menu items are settable. Finally, by actuating the mode key it is possible to confirm or to take over, respectively, a set parameter and to come back into that submenu in which menu items are selectable, in order to set additional parameters.

According to one embodiment, upon actuation of the parameter key, the control unit controls the changeover from a submenu concerning one certain mode of operation of the metering apparatus into a submenu concerning the same mode of operation with selectable menu items and/or the start of metering processes in the mode of operation of the aforesaid submenu and/or the start of metering processes in a certain mode of operation which corresponds to a selected menu item of the main menu. Thus, by actuating the parameter key, it is possible to select menu items and/or to start metering processes departing from a submenu concerning a certain mode of operation. Further, directly after selecting modes of operation in the main menu, the respective modes of operation can be started by pushing the parameter key.

According to one embodiment, upon actuation of the control keys, the control unit controls the movement of a pointer to different menu items in the main menu, and/or the movement of the pointer to different menu items in a submenu concerning a certain mode of operation with selectable menu items, and/or the adjustment of the parameter in a submenu in which the parameter of a selected menu item is settable, and/or the movement of the displacer element after the start of the metering operation. Through this, the navigation in the menus and the control of the dislocation of the displacer device is controlled in a simple manner. The pointer appears in the display of the display device. Here, it is directed to one certain menu item at a time. For instance, it is realised as an arrow or another graphic symbol. In addition or instead of a pointer, the menu item can be accentuated, for instance by a strongly contrasting representation, a representation in another colour, by underlining and so on.

For instance, the control keys are formed by a pair of keys arranged next to each other, which can be actuated independently. For instance, the simultaneous actuation of two control keys can be regarded as an erroneous actuation by the control unit, which remains without consequences. According to one embodiment, the control keys can be actuated by a rocker key in one or the other direction, so that erroneous actuations can be excluded. Further, navigation in the menus, setting parameters and dislocating the displacer element in the upward and downward direction can be controlled in a particularly obvious way by means of the rocker key.

Particularly user-friendly is an embodiment, wherein the control unit controls the display of the respective functions of the mode key and of the parameter key by means of the display device. For example, in this embodiment, the display device indicates when it is possible to select a submenu by actuating the mode key and to start a metering process in a certain mode of operation by actuating the parameter key.

In principle, it is possible that after actuation of a control key, the control unit controls the dislocation of the displacer element of the displacer device as long as the release of the dislocation is stopped by the actuation of another key. According to a particularly user-friendly embodiment, the control unit controls the dislocation of the displacer element of the displacer device as long as the push at one of the control keys lasts and it stops the dislocation of the displacer element as long as the control keys are released.

According to one embodiment, one control key has a second switching point, and upon actuation of the control key, the control unit controls the dislocation of the displacer element of the displacer device up to reaching the second switching point such that the displacer element executes an overblow stroke. Through this, the intentional execution of the overblow stroke is facilitated for the user.

According to one embodiment, the metering apparatus is a single or multi channel metering apparatus. A single channel metering apparatus co-operates with one single pipette point or syringe. A multichannel metering apparatus co-operates with several pipette points or syringes. Multichannel metering apparatuses can have one single displacer device, which can be communicatingly connected to several pipette points. But they can also have plural displacer devices, wherein each displacer device communicates with one pipette point.

According to a user-friendly embodiment, the metering apparatus has a display device in a housing head of the housing and the mode key, the parameter key and the pair of control keys below the display device. This arrangement permits a good recognisability of the display device through the user and a simple actuation of the operational controls.

According to one embodiment, the metering apparatus has a longitudinal housing shaft and a housing head angled with respect to the former. Arrangement of the display device and the operational controls at the upper side of the housing head is particularly advantageous for the user.

According to one embodiment which is particularly user-friendly, the mode key and the parameter key are arranged next to each other, and/or the control keys are arranged on top of each other. According to a further embodiment, at least one control key is arranged between the mode key and the parameter key. According to a further embodiment, a discarder key is arranged below the mode keys. The aforementioned embodiments facilitate the operation of the operational controls by one hand or the thumb of one hand, respectively, because all the aforementioned operational controls are in the reach of the thumb of that hand which holds a housing shaft of the metering apparatus. For this purpose, the operational controls are preferably arranged in the connecting region between a housing head and the housing shaft.

According to a further embodiment, that control key which is arranged next to the holding device has the second switching point for triggering the overblow stroke. Thus, this control key points obviously into that direction in which the overblow stroke is executed.

BRIEF DESCRIPTION OF SEVERAL VIEWS OF THE DRAWINGS

The present invention will be explained in more detail by means of the attached drawings of embodiments in the following. In the drawings show:

FIG. 4 the display device of the metering apparatus in different operational situations in a schematic top view;

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated According to FIG. 1 to 3, a metering apparatus 1 has a housing 2 realised as a handle, with a longitudinal housing shaft 3 and a housing head 4 angled at about 45° on the upper end. The housing 2 has a cone 5 at the lower end for putting up a pipette point 6.

Figure 1:
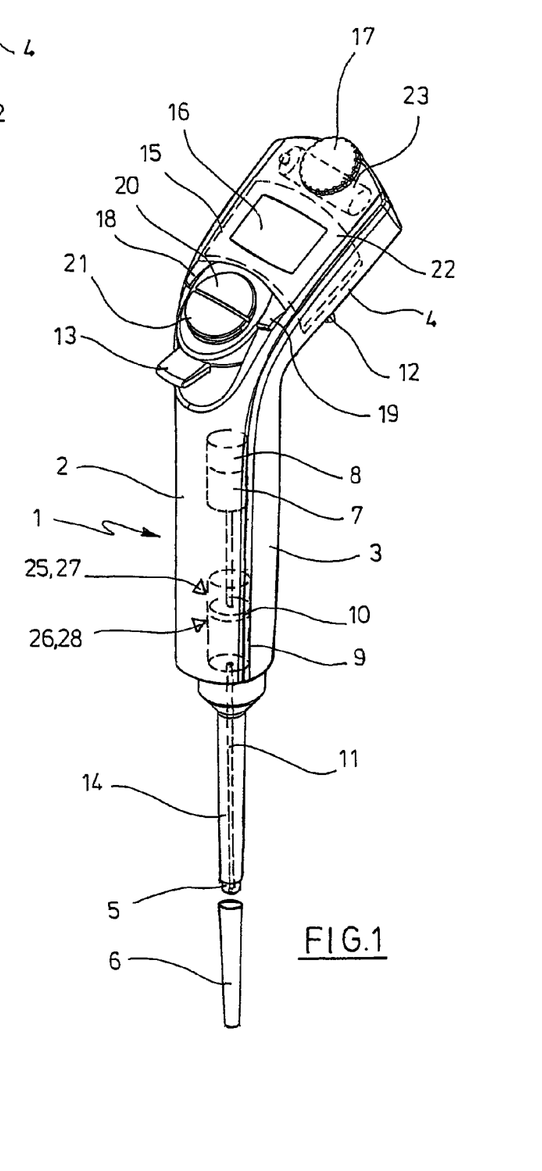
FIG. 1 an electronic metering apparatus in a perspective view, skew from the front and from the side.
Figure 2:
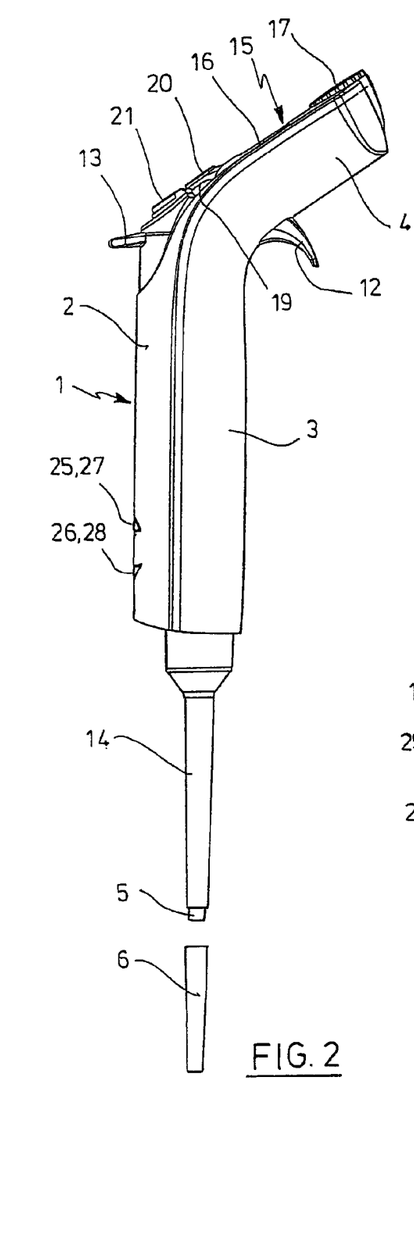
FIG. 2 the same metering apparatus in a view from the side.
Figure 3:
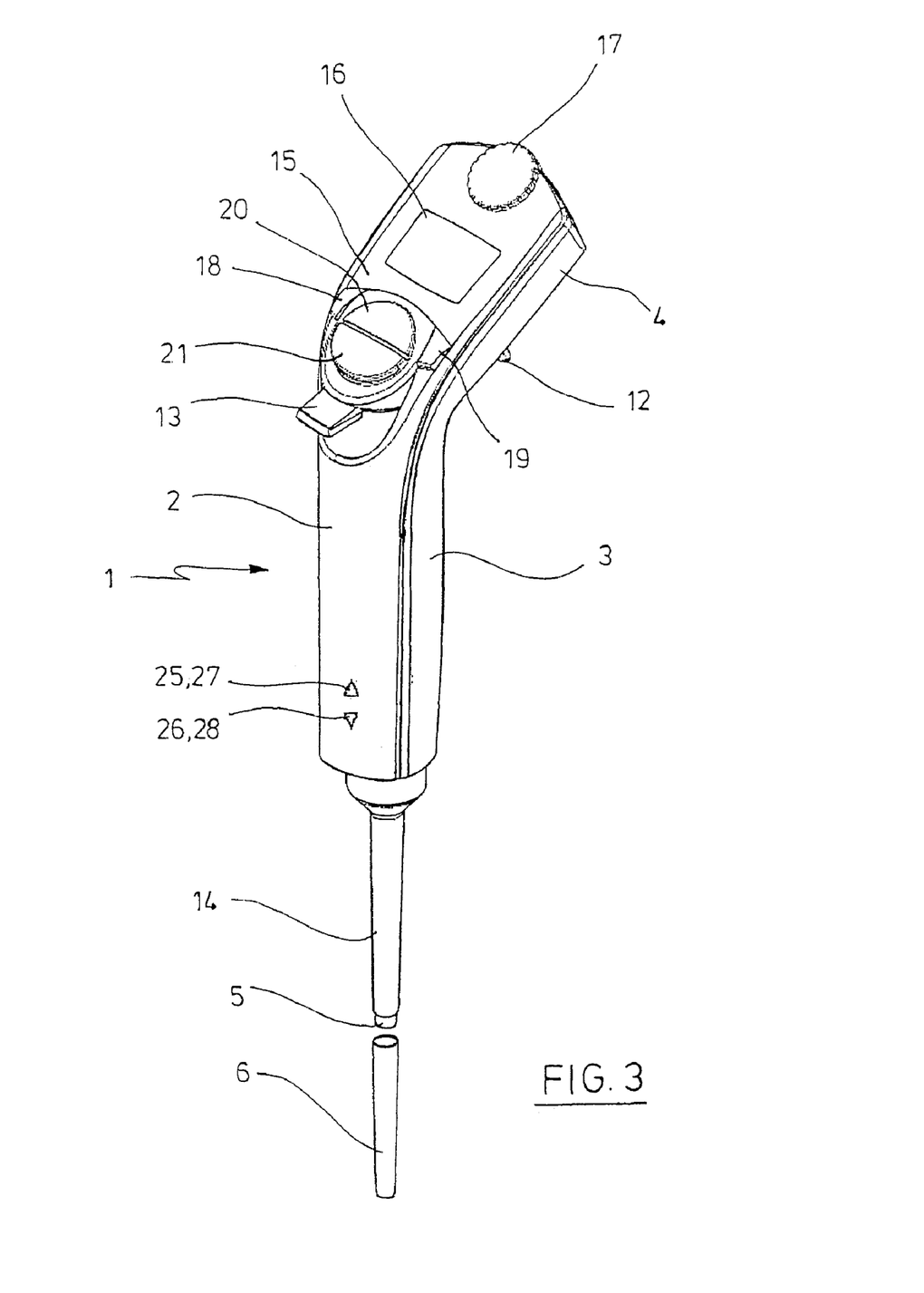
FIG. 3 the same metering apparatus in the same perspective view as in FIG. 1, but without depiction of inside-situated components.

In the housing shaft 3, a drive 7 with an electric motor 8 is arranged. Further, there is a cylinder 9 with a longitudinally movable plunger 10 arranged therein, which is mechanically connected with the drive 7. Via a connecting channel 11, the cylinder is connected to an opening at the end of the cone 5.

On its downside, the housing head 4 has a downward bent hook 12, which facilitates securely holding the metering apparatus 1 on the housing shaft 3.

At the upper end of the housing shaft 3, a discarder key 13 is arranged, which is mechanically connected with a discarder sleeve 14, so that upon actuation of the discarder key 13, a pipette point 6 can be pushed off from the cone 5.

On the top side 15 or the front side of the housing head 4, respectively, there is a display device 16 or a display, respectively, which is realised as a LCD-Display, for instance. Above the display device 16, there may be a setting button 17 for rapid setting of the mode of operation.

Below the display device 16, a mode key 18 and a parameter key are arranged next to each other. Between them, there are two control keys 20, 21 on top of each other, wherein the upper control key 20 controls an upward movement and the lower control key 21 controls a downward movement and an overblow stroke.

The control key 20 has only one single switching point. The control key 21 has two switching points, wherein reaching the first switching point triggers the downward movement and reaching the second switching point triggers an overblow stroke of the plunger 10.

In the housing head 4, an electric control unit 22 is arranged on a circuit board, which is connected with the electric motor 8, the display device 16 and the keys 18 to 21. Preferably, the electric control unit 22 comprises an electronic data processing unit, a microcontroller for instance.

Further, an electric power supply 23 is present in the housing head 4, which is formed by several accumulators for instance, which can be charged by means of an external charger. The electric power supply 23 supplies the electric component parts of the metering apparatus 1 with electric current.

From a standby mode, into which it falls after a certain idle period, the electronic metering apparatus 1 can be brought into the normal operating condition by actuating an arbitrary key 18 to 21. In addition or instead of this, a not shown on/off-switch can be present for switching on the normal operating condition or switching it off, respectively.

Figure 41:
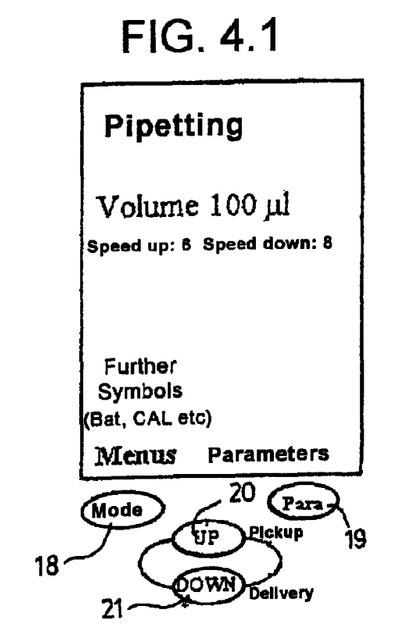

After switching on, the display device shows a submenu with the lastly set mode of operation and the lastly set parameters of this mode of operation. In FIG. 4.1, this is shown for the case that the mode of operation "pipetting" had been lastly set.

Figure 42:
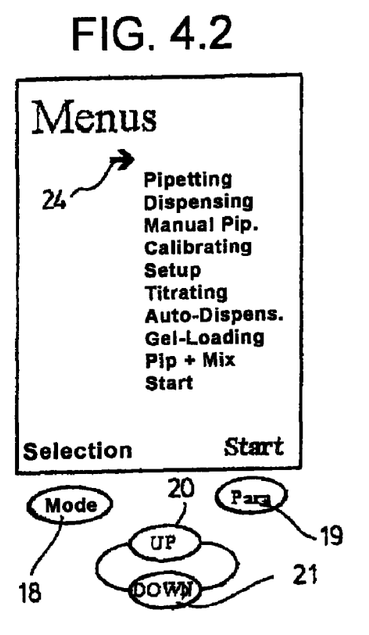

After actuation of the parameter key 19, it is possible to change parameters of this mode of operation. The display after actuation of the parameter key 19 is shown in FIG. 4.2. In this display, there is a pointer 24, which can be shifted upward and downward by means of the control keys 20, 21.

Figure 43:
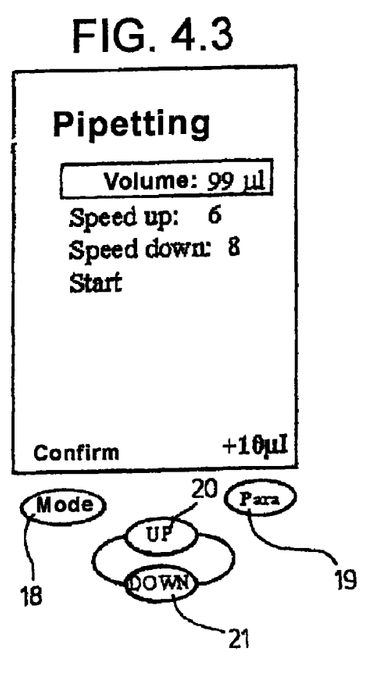

The parameter towards which the pointer 24 in FIG. 4.2 points can be changed after the actuation of the mode key 18. The change of the parameter takes place by actuating the control keys 20, 21, as is shown in FIG. 4.3. The change of this parameter is confirmed by the actuation of the mode key 18.

Thereafter, according to FIG. 4.2, by means of the control keys 20, 21, the pointer 24 can be adjusted to a further parameter in order to change it.

When all the settable parameters have the desired values, pipetting is started by actuating the parameter key 19.

The upward and downward movement of the plunger 10 is controlled by actuating the control keys 20, 21.

After the end of the pipetting process, the submenu for the set metering operation with the set parameters is shown, as is represented in FIG. 4.1.

From this condition, the user reaches a main menu shown in FIG. 4.4 by actuating the mode key 18. In this, all the modes of operation are indicated.

By actuating the control keys 20, 21, the pointer can be set to a certain mode of operation. By actuating the mode key 18, the menu is invoked in which the respective mode of operation with the effective parameters is shown. Departing from this condition, the parameters can be set, as this has been described above for the mode of operation "pipetting". In order to start the respective mode of operation, the parameter key 18 is pushed again.

It is also possible to start the mode of operation to which the pointer 24 points directly from the main menu according to FIG. 4.4, by actuating the parameter key 19.

Further, there is at any time the possibility for the user to set a mode of operation rapidly by actuating the setting button 17. Thereafter, the corresponding submenu appears promptly on the display of the display device 16. For the rest, the setting of the mode of operation via the electric operational controls 18 to 21 precedes the setting via the setting button 17.

In the lower row of the display device 16, the respective actual functions of the mode key 18 and the parameter key 19 are shown in the respective main- and submenus.

According to FIG. 1 to 3, at the bottom end of the housing shaft 3, two LED's 25, 26 are arranged, which are covered by windows 27, 28 of transparent plastic material in a triangular shape. The tips of the windows 27, 28 point into different directions.

The LED's 25, 26 are also electrically connected with the electric control unit 22.

In the operation of the metering apparatus 1, the LED's 25, 26 always indicate the next reasonable dislocation of the plunger 10. When a dislocation of the plunger 10 towards the upside is reasonable for picking up liquid, the LED 25 below the window 27 lights up. When liquid has to be delivered, and correspondingly the plunger 10 must move downward, the LED 25 below the window 28 lights up.

Figure 5:
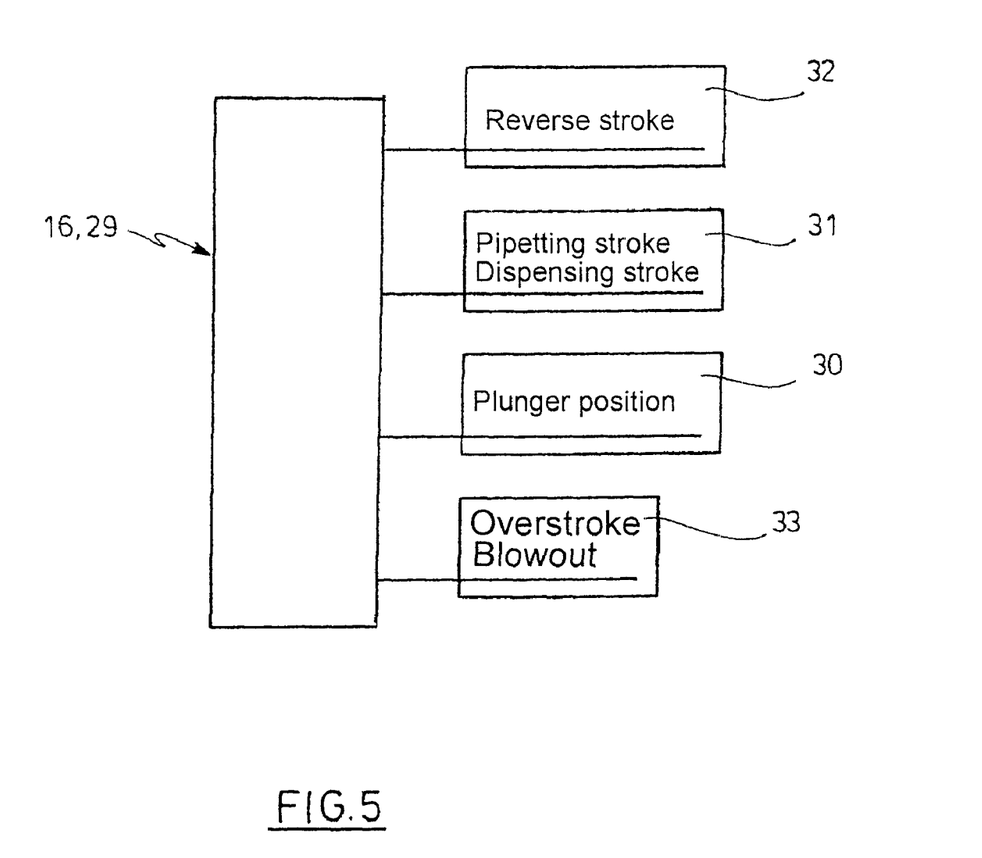
FIG. 5 a display device in a schematic top view.

FIG. 5 shows the display device 16 in the previously described metering apparatus 1 or the display device 29 of another metering apparatus, which has at the bottom end of the housing shaft 3 in addition to or instead of the LED's 25, 26 a display device which permits a corresponding indication. At the bottom end of the housing shaft 3, the display device 29 may be present in addition to the display device 16 or instead of the display device 16.

The display according to FIG. 5 is realised by means of a LCD, of an OLED or like a bar diagram in old hi-fi systems, for instance.

The position of the plunger is indicated by a direction arrow 30. This may take place in relation to the set maximum volume (e.g., upper limit=5×100 µl=500 µl at a 1200 µl-pipette) or absolutely with respect to the plunger position (thus, at 6×100 µl=600 µl in the centre of the display) (display region 31). It is also possible to depict the reverse stroke (display region 32) and the overstroke or blowout, respectively (display region 33) (by colour, graphically or distinguished in any other way).

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An electronic metering apparatus for metering liquids the apparatus having
   a longitudinal, handleable housing (2);
   a drive (7), arranged in the housing (2), with an electric motor (8);
   at least one displacer device (9, 10), connected to the housing (2), with a displacer element (10), which is connected to the drive (7);
   at least one holding device (5) on the bottom end of the housing (2) for holding a metering device selected from the group consisting of a pipette point (6) and a syringe;
   at least one electric operational control (18 to 21) connected to the housing (2);
   at least one electric information device (25, 26) connected to the housing (2);
   an electric control unit (22) arranged in the housing (2), which is connected to the electric motor (8), the electric operational control (18 to 21) and the electric information device (25, 26), and which controls the information device (25, 26) depending on the position and/or previous changes of the position of the displacer element (10), in order to put out an information concerning the next reasonable dislocation of the displacer element (10);
   and an electric power supply (23);
   wherein the electric operation control (18 to 21) comprises a pair of electric control keys (20, 21) for controlling the dislocation of the displacer element (10), wherein the two control keys (20, 21) control the dislocation of the displacer element (10) in different directions.

2. A metering apparatus according to claim 1, wherein the displacer device (9, 10) comprises a cylinder (9) with a plunger (10) arranged to be movable alongside therein.

3. A metering apparatus according to claim 1, wherein the information device (25, 26) comprises at least one electric-optic unit.

4. A metering apparatus according to claim 3, wherein the information device (25, 26) comprises at least one electric light source.

5. A metering apparatus according to claim 1, which has an electric-optic display device (16) with a display surface observable from the outside.

6. A metering apparatus according to claim 5, wherein the information device is the display device.

7. A metering apparatus according to claim 1, which has an angled housing head (4) on the upper end of a longitudinal housing shaft (3) and which has the electric operational control (18 to 21) and/or the electric display device (16) on the housing head (4).

8. A metering apparatus according to claim 1, with an electric mode key (18) and an electric parameter key (19) for changeover between different menus, wherein the two control keys (20, 21) are arranged next to each other and further control the navigation in the menus and the setting of parameters, an electric display device (16) for displaying menus and parameters, wherein the electric control unit (22) is connected to the electric mode key (18), the electric parameter key (19), the electric control keys (20, 21) and the electric display device (16), and controls the display of menus and parameters by the display device (16) as well as the dislocation of the displacer element (10) corresponding to the actuation of the mode key (18), the parameter key (19) and the control keys (20, 21).

9. A metering apparatus according to claim 8, wherein the control unit (22) controls the indication by the display device (16) of submenus concerning certain modes of operation of the metering apparatus and of a main menu, comprising plural modes of operation, corresponding to the actuation of the mode key (18) and the parameter key (19).

10. A metering apparatus according to claim 8, wherein upon actuation of the mode key (18), the control unit (22) controls the changeover from a submenu concerning one certain mode of operation of the metering apparatus into a main menu concerning plural modes of operation of the metering apparatus and/or the changeover from the aforementioned main menu into a submenu concerning a certain mode of operation of the metering apparatus with selectable menu items and/or the changeover from the aforesaid submenu into a submenu concerning the same mode of operation, in which the parameter of a selected menu item can be set, and/or the changeover with transfer of a set parameter from the aforesaid submenu into the submenu concerning the same mode of operation with selectable menu items.

11. A metering apparatus according to claim 8, wherein upon actuation of the parameter key (19), the control unit (22) controls the changeover from a submenu concerning one certain mode of operation of the metering apparatus into a submenu concerning the same mode of operation with selectable menu items and/or the start of metering processes in the mode of operation of the aforesaid submenu and/or the start of metering processes in a mode of operation which corresponds to a selected menu item of the main menu.

12. A metering apparatus according to claim 8, wherein upon actuation of the control keys (20, 21), the control unit (22) controls the movement of a pointer (24) to different menu items in the main menu, and/or the movement of the pointer to different menu items in a submenu concerning a certain mode of operation with selectable menu items, and/or the adjustment of the parameter in a submenu in which the parameter of a selected menu item is settable, and/or the movement of the displacer element (9) after the start of a metering process.

13. A metering apparatus according to claim 8, wherein the control keys (20, 21) are realised as rocker key.

14. A metering apparatus according to claim 8, wherein the control unit (22) controls the display of the respective function of the mode key (18) and/or the parameter key (19) and/or the control keys (20, 21) by means of the display device (16).

15. A metering apparatus according to claim 8, wherein the control unit (22) controls the dislocation of the displacer element (9) of the displacer device (9, 10) as long as the push at one of the control keys (20, 21) lasts and it stops the dislocation of the displacer element (9) as long as the control keys (20, 21) are released.

16. A metering apparatus according to claim 8, wherein one of the two electric control keys (21) has a second switching point, the electric control unit (22) ordering the execution of an overblow stroke by the displacer element (10) when the second switching point is reached.

17. A metering apparatus according to claim 8, which has a display device (16) in a housing head (4) of the housing (3) and the electric mode key (18) and/or the electric parameter key (19) and/or the electric control keys (20, 21) below the display device (16).

18. A metering apparatus according to claim 8, wherein the mode key (18) and the parameter key (19) are arranged next to each other, and/or the control keys (20, 21) are arranged on top of each other.

19. A metering apparatus according to claim 8, wherein at least one control key (20, 21) is arranged between the mode key (18) and the parameter key (19).

20. A metering apparatus according to claim 8, wherein a discarder key (13) is arranged below the mode key (18) and/or the parameter key (19) and/or the control keys (20, 21).

21. A metering apparatus according to claim 8, wherein the mode key (18), the parameter key (19) and the control keys (20, 21) are arranged on the topside of a connecting region between the longitudinal housing shaft (3) and the housing head (4) angled with respect to the same.

22. A metering apparatus according to claim 21, in wherein the discarder key (13) is arranged in the connecting region between the housing shaft (3) and the housing head (4).

23. A metering apparatus according to claim 1, which is a single or multi channel metering apparatus.

24. A metering apparatus according to claim 1, wherein that control key (21) which is arranged next to the holding device (5) has the second switching point for triggering the overblow stroke.

* * * * *